(12) United States Patent
Makihara et al.

(10) Patent No.: US 7,025,870 B2
(45) Date of Patent: Apr. 11, 2006

(54) METHOD FOR ANALYZING THE OXYGEN CONCENTRATION OF A GAS

(75) Inventors: Akira Makihara, Osaka (JP); Yoshiro Matsumoto, Osaka (JP); Ken Ohmae, Osaka (JP)

(73) Assignee: Osaka Sanso Kogyo Ltd., Osaka (JP)

( * ) Notice: Subject to any disclaimer, the term of this patent is extended or adjusted under 35 U.S.C. 154(b) by 548 days.

(21) Appl. No.: 10/232,829

(22) Filed: Sep. 3, 2002

(65) Prior Publication Data
US 2003/0101795 A1 Jun. 5, 2003

(30) Foreign Application Priority Data
Nov. 30, 2001 (JP) .............................. 2001-365980

(51) Int. Cl.
*G01N 27/26* (2006.01)

(52) U.S. Cl. .................................... 205/785.5; 436/136

(58) Field of Classification Search ................ 436/136, 436/138; 73/1.06, 1.07; 204/431, 432, 424, 204/409; 205/785.5, 782, 782.5
See application file for complete search history.

(56) References Cited

U.S. PATENT DOCUMENTS 5,239,856 A * 8/1993 Mettes et al. ................. 73/1.05
5,542,284 A     8/1996 Layzell et al.
5,569,838 A * 10/1996 Broedel et al. ............ 73/23.31
5,691,464 A    11/1997 Cao

FOREIGN PATENT DOCUMENTS

JP          5-17640         5/1993
JP          3172571         3/2001

* cited by examiner

*Primary Examiner*—Kaj K. Olsen
(74) *Attorney, Agent, or Firm*—Roylance, Abrams, Berdo & Goodman, L.L.P.

(57) ABSTRACT

A method for analyzing the oxygen concentration of a gas with an oxygen concentration analyzer of such a type that a probe sensor, when supplied with a gas to be analyzed, produces an electrical output which is proportional to the concentration of oxygen in the gas, comprising the steps of preparing a first gas mixture in which an oxygen-free gas and a sample gas are mixed at a certain flow ratio and a second gas mixture in which the oxygen-free gas and the sample gas are mixed at a different flow ratio than in the first gas mixture, passing the first gas mixture and the second gas mixture asynchronously into the probe sensor, and comparing the electrical outputs from the sensor for the first gas mixture and the second gas mixture, as well as the proportions of the flow of the sample gas in the first gas mixture and the second gas mixture to thereby calculate the oxygen concentration in the sample gas. The method eliminates the need to perform frequent zero adjustment and enables the oxygen concentration in the sample gas to be measured with consistent results.

8 Claims, 5 Drawing Sheets

METHOD FOR ANALYZING THE OXYGEN CONCENTRATION OF A GAS

BACKGROUND OF THE INVENTION

This invention relates to a method for analyzing the concentration of oxygen in various gases, particularly to a method for analyzing trace (sub-ppb) levels of oxygen concentration.

A known type of oxygen concentration analyzer is such that a probe sensor, when supplied with a gas to be analyzed, produces an electrical output which is proportional to the concentration of oxygen in the gas. In a version of this type, oxygen in the gas reacts with water in the electrolyte on the surface of an electrode in the probe sensor to generate hydroxyl ions which migrate to the other electrode across the electrolyte, whereupon an electric current flows in a quantity proportional to the oxygen concentration in the gas. This operating principle is used by a Galvanic cell type oxygen concentration analyzer.

A conventional type of oxygen concentration analyzer which produces a current or other electrical output proportional to the concentration of oxygen in the gas to be analyzed is shown schematically in block form in FIG. 4. The analyzer has two gas feed lines, one of which is supplied with an oxygen-free gas (hereunder referred to as a zero gas) and the other line with a gas of a known oxygen concentration (which is hereunder referred to as a standard gas) and a sample gas. The sample gas and the standard gas are selectively supplied at separate lines via switch valves 1 and 2. The feed line for the zero gas has a switch valve 3 and the feed line for the sample gas or standard gas has a switch valve 4 and by selectively opening these valves, either the zero gas or the sample or standard gas will be fed to a flow regulator which controls the gas to flow to the probe sensor at optimum rate.

The analyzer contemplated by the invention determines the oxygen concentration using a calibration curve according to the following principle. The calibration curve is a straight line on a graph that represents a proportional expression describing the relationship between the oxygen concentration in a gas and a current or other electrical output of the probe sensor. An example of the calibration curve is shown in FIG. 2. The variable x on the horizontal axis represents the oxygen concentration in the sample gas, the variable y on the vertical axis represents the sensor output, a represents the slope of the calibration curve, and b represents the height at which the calibration curve intercepts the vertical axis. The first step of measurement is to determine the mathematical expression for the calibration curve, $y=ax+b$. To this end, the zero gas is first passed into the sensor and the sensor output (b) is determined (since the sensitivity of the sensor varies with ambient temperature and other factors, the output ($y=b$) for the zero gas ($x=0$) does not necessarily register zero). Then, the standard gas is passed into the sensor to determine the output ($y_1$) for a known oxygen concentration ($x_1$). Suppose here that b is 100 µA, $x_1$ is 10 ppb and $y_1$ is 200 µA. Substituting these values into $y=ax+b$, we obtain $200=10a+100$. Since $a=10$, the calibration curve is expressed by $y=10x+100$.

In the next step, a sample gas of an unknown oxygen concentration is passed into the sensor. If the sensor output (y) is 150 µA, $150=10x+100$, so the oxygen concentration (x) in the sample gas is determined as 5 ppb.

The actual measurement of oxygen concentration starts with passing the zero gas into the sensor which produces an output to be represented on the display in the analyzer. If the sensor output is not zero (if b is 100 µA as in the illustrated case), the correction dial is rotated so that the sensor output reads zero (this correction is hereunder referred to as zero adjustment and as the result of zero adjustment, the calibration curve can be expressed by $y=ax$). In the next step, the standard gas is passed into the sensor and the output y is determined. Since x is a known value, the slope of the calibration curve (a) is determined and the concentration span is adjusted. To be more specific, an adjustment is made such that the sensor output takes a specified value that corresponds to the known oxygen concentration in the standard gas. Subsequently, the sample gas is passed into the sensor and the sensor output can be converted to the oxygen concentration in the sample gas.

Thus, in the prior art method, the zero gas, the standard gas and the sample gas are sequentially passed into the sensor by switching one gas to another. If the sensor output has not completely stabilized, zero adjustment has to be made. Even if the sensor output completely stabilizes after zero adjustment, it may occasionally vary due to ambient temperature or other factors, potentially causing the display in the analyzer to register a negative output for the sample gas. The sensor output for the sample gas can also drop if the sensor performance deteriorates with time on account, for example, of a drop in reactivity on the electrode surface in the sensor or of a drop in ion mobility due to stained electrolyte. The effects of ambient temperature and other factors are particularly significant when trace (sub-ppb) levels of oxygen concentration are to be measured with a Galvanic cell type analyzer.

In order to solve these problems, the gas to be flowed into the sensor is frequently switched from the sample gas to the zero gas and zero adjustment is made. Of course, the sample gas cannot be analyzed as long as zero adjustment is performed but this is not desirable in facilities that perform continuous measurement of trace (sub-ppb) levels of oxygen concentration (e.g. a gas control facility which performs continuous analysis and monitoring of the oxygen concentration in the exit gas from a high-purity gas refinery or a facility which performs continuous analysis and monitoring of the oxygen concentration in an inert gas feed gas and a carrier gas to a semiconductor fabrication plant) because any sudden change in oxygen concentration that occurs in these facilities must be measured without time delay. As a further problem, when the sample gas is switched over to the zero gas to start zero adjustment, not only the zero gas but also the sample gas in a sump on the gas feed line tends to be introduced into the sensor; as a result, the time required to stabilize the zero point is prolonged, making it difficult to perform efficient zero adjustments.

SUMMARY OF THE INVENTION

An object, therefore, of the present invention is to provide a method of analyzing oxygen concentration that eliminates the need to perform frequent zero adjustment during analysis and which enables the oxygen concentration in a sample gas to be measured at all times in a consistent manner.

Another object of the invention is to provide an analyzer for implementing the method.

The first object of the invention can be attained by a method for analyzing the oxygen concentration of a gas with an oxygen concentration analyzer of such a type that a probe sensor, when supplied with a gas to be analyzed, produces an electrical output which is proportional to the concentration of oxygen in the gas, comprising the steps of:

preparing a first gas mixture in which a zero gas (oxygen-free gas) and a sample gas are mixed at a certain flow ratio and a second gas mixture in which the zero gas and the sample gas are mixed at a different flow ratio than in the first gas mixture;

passing the first gas mixture and the second gas mixture asynchronously into the probe sensor; and comparing the electrical outputs from the sensor for the first gas mixture and the second gas mixture, as well as the proportions of the flow of the sample gas in the first gas mixture and the second gas mixture to thereby calculate the oxygen concentration in the sample gas.

The second object of the invention can be attained by a an oxygen concentration analyzer of such a type that a probe sensor, when supplied with a gas to be analyzed, produces an electrical output which is proportional to the concentration of oxygen in the gas, comprising:

a line for feeding a zero gas and a line for selectively feeding a gas of a known oxygen concentration and a sample gas;

a gas flow controller provided on each of said lines to control the gas flow to a specified value;

a mixer in which the gases fed from the two lines via the gas flow controllers are mixed at a specified flow ratio; and a probe sensor that determines the oxygen concentration in the gas being fed via the mixer.

DETAILED DESCRIPTION OF THE INVENTION

The oxygen concentration analyzer to be used in the invention is of such a type that the probe sensor, when supplied with a gas to be analyzed, produces an electrical output which is proportional to the concentration of oxygen in the gas and various versions operating on various principles are included, such as a zirconia type oxygen concentration analyzer, a yellow phosphorus luminescence type oxygen concentration analyzer and a Galvanic cell type oxygen concentration analyzer.

Figure 2:
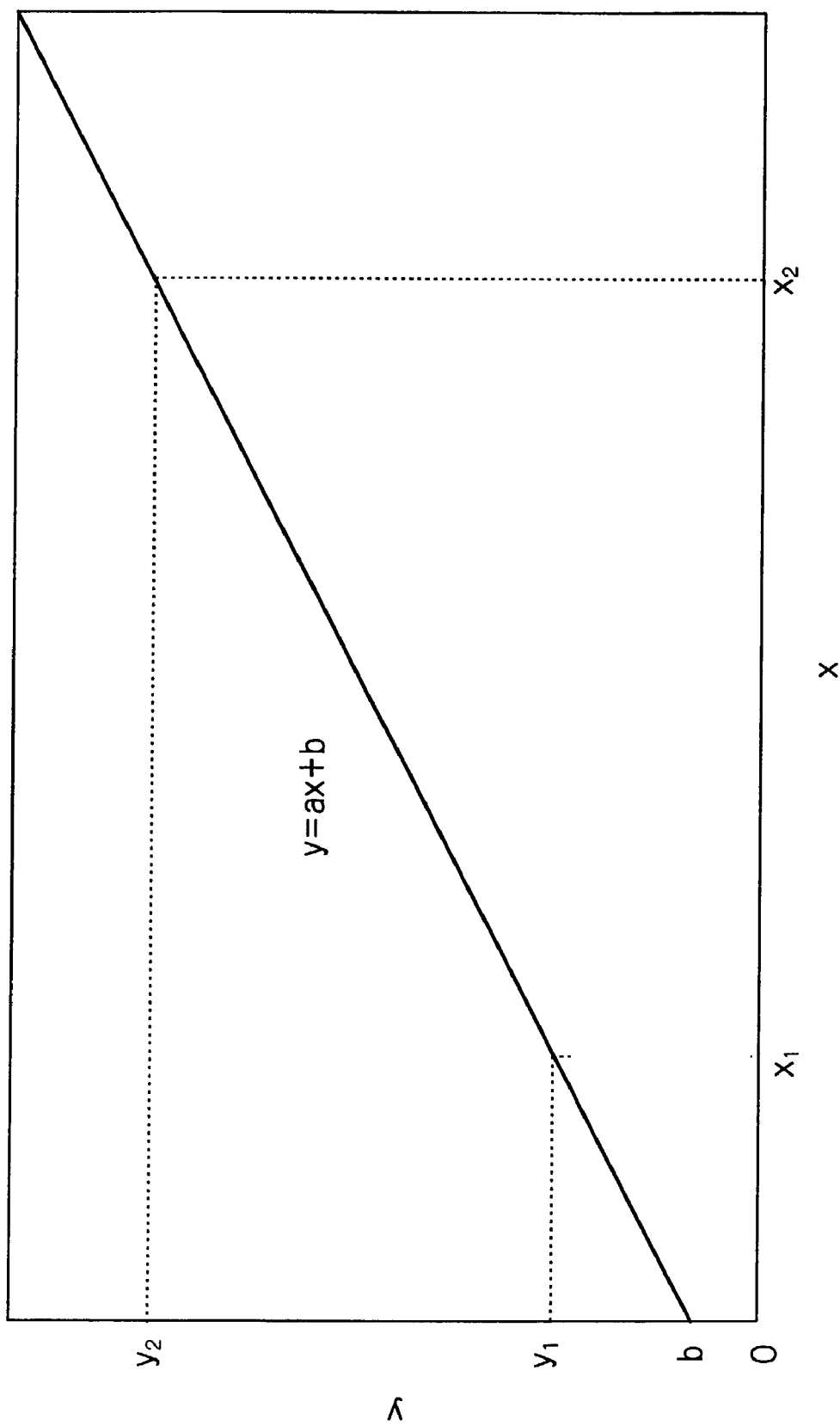
FIG. 2 is a graph on which a proportional expression describing the relationship between the oxygen concentration in a gas and an electrical output from a probe sensor is represented by a straight line.

The operating principle for the analyzing method of the invention is described below. As already mentioned, the calibration curve for the sample gas is expressed by $y=ax+b$, in which x, y, a and b have the meanings defined above. Write $y_1$ for the sensor output produced when the oxygen concentration in the first gas mixture (see above) is $x_1$ and also write $y_2$ for the sensor output produced when the oxygen concentration in the second gas mixture is $x_2$ (see FIG. 2). Thus, $$y_1 = ax_1+b,\ y_2 = ax_2+b,$$

$$y_1-y_2 = (ax_1+b)-(ax_2+b) = a(x_1-x_2)$$

$$x_1-x_2 = (y_1-y_2)/a \quad (1)$$

As the result of mixing the sample gas with the zero gas, the oxygen in the sample gas is diluted to give a lower oxygen concentration but the oxygen content does not change since no oxygen is contained in the zero gas. Therefore, the oxygen content in the sample gas which is the product of the flow of the sample gas and the oxygen concentration in it (x) is equal to the oxygen content in the first gas mixture which is the product of the flow of the first gas mixture and the oxygen concentration in it ($x_1$). Thus, (flow of first gas mixture)$x_1$=(flow of sample gas)$x$ $x_1 = x$(flow of sample gas/flow of first gas mixture)
   $= xS_1$ Since the same discussion holds for the second gas mixture, $x_2 = x$(flow of sample gas/flow of second gas mixture)
   $= xS_2$ Eq. 1 can be rewritten as $$y_1-y_2 = a(x_1-x_2) = a(xS_1-xS_2) = ax(S_1-S_2)$$

hence, $x = (y_1-y_2)/a(S_1-S_2)$

Since a is the slope of the calibration curve, the value of x does not change if $(y_1-y_2)$ in the above equation is rewritten as $(y_2-y_1)$ and $(S_1-S_2)$ as $(S_2-S_1)$ Hence, the following equation including absolute values also holds:

$$x = |y_1-y_2|/a|S_1-S_2| \quad (2)$$

In Eq. 2, $y_1$ and $y_2$ represent electrical outputs of the probe sensor, a can be preliminarily determined using the zero gas and the standard gas as described in connection with the prior art, and $S_1$ and $S_2$ can be set at desired values by means of the flow controllers. Eq. 2 states that $|y_1-y_2|$, or the absolute value of the difference between the electrical output ($y_1$) produced when the first gas mixture is passed into the sensor and the electrical output ($y_2$) produced when the second gas mixture is passed into the sensor, is proportional (with proportionality constant of a) to $|S_1-S_2|$, or the absolute value of the difference between $S_1$ which is the proportion of the flow of the sample gas in the first gas mixture and $S_2$ which is the proportion of the flow of the sample gas in the second gas mixture; substituting these absolute values into Eq. 2, one can calculate the oxygen concentration (x) in the sample gas. This means there is no need to determine the sensor output (b) for the zero gas, i.e., no need to perform zero adjustment. In other words, the method of the invention theoretically has no need to correct or modify the calibration curve by performing zero adjustment as in the prior art. As a result, frequent zero adjustment is eliminated from the analysis of oxygen concentration in the sample gas and it can be measured for an extended period without interruption.

A configuration of the oxygen concentration analyzer of the invention operating on the principle described above is shown in block form in FIG. 1. The analyzer has two gas feed lines, one of which is supplied with the zero gas and the other supplied with the standard gas and the sample gas. The sample gas and the standard gas are selectively supplied at separate lines via switch valves 1 and 2. A flow controller A is provided on the zero gas feed line and a flow controller B is provided on the sample gas/standard gas feed line so that the flow of the zero gas and the flow of the standard gas or the sample gas can be adjusted to desired values. A controlled flow of the zero gas is mixed with a controlled flow of the standard gas or the sample gas in a mixer, from which a gas mixture of an adequately uniform concentration emerges and flows into an oxygen concentration analyzing probe sensor. The function of the mixer is to mix gases in desired proportions and bring the mixture to have a uniform concentration. In a preferred embodiment of the mixer, a static mixer that forcibly mixes two fluids by mechanical means is inserted into a pipe; alternatively, the mixer may comprise a pipe having a sufficient diameter and length to ensure that two fluids introduced into it are mixed by the action of turbulence and a nozzle inserted into the pipe in order to supply it with the fluids.

Figure 1:
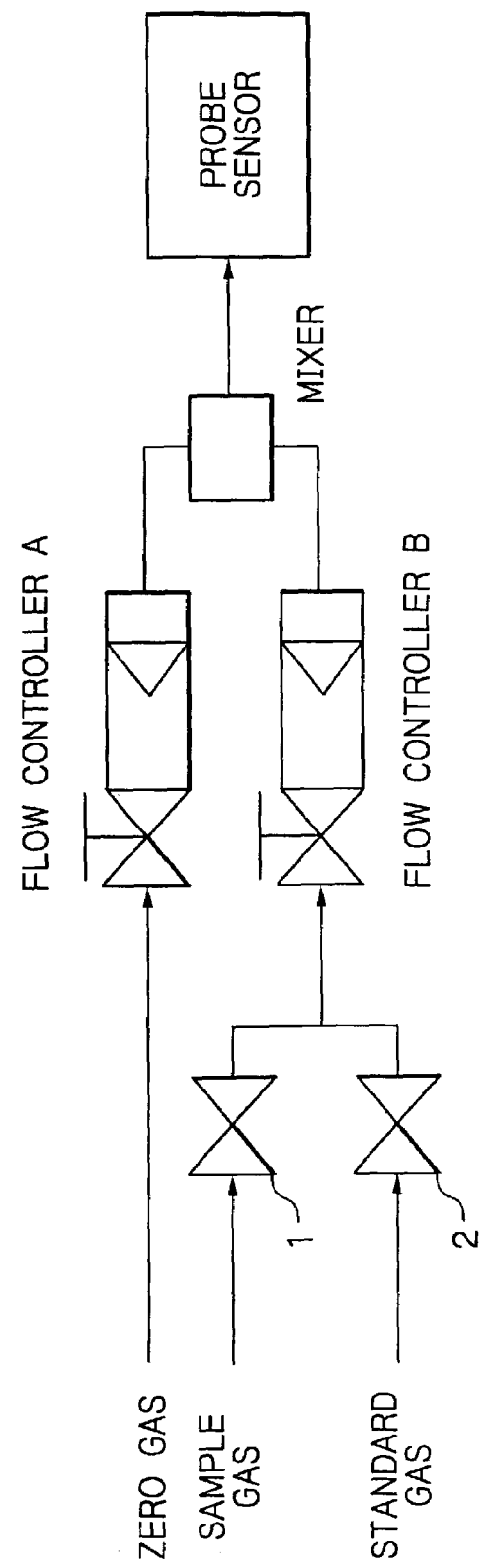
FIG. 1 is a block diagram showing the configuration of the oxygen concentration analyzer of the invention.

To measure oxygen concentration with the system shown in FIG. 1, the zero gas is first passed into the sensor which produces an output (e.g. an electric current) to be represented on the display in the analyzer. If the sensor output is not zero, an adjustment is made so that the sensor output reads zero (zero adjustment). In the next step, the standard gas is passed into the sensor and the output is determined to adjust the concentration span. To be more specific, an adjustment is made such that the sensor output takes a specified value that corresponds to the known oxygen concentration in the standard gas. The method of adjustment is the same as described in connection with the prior art. What follows is the first stage, in which the zero gas is mixed with a certain flow of the sample gas to make the first gas mixture which is passed into the probe sensor and its output is determined. In the second stage, the zero gas is mixed with a different flow of the sample gas than in the first stage to make the second gas mixture which is also passed into the probe sensor and its output is determined. The flow ratio between the sample gas and its mixture with the zero gas as measured in each of the first and second stages and the sensor outputs are input into a computer which calculates the oxygen concentration in the sample gas by Eq. 2. Briefly, two stages are consecutively performed with the flow ratio between the sample gas and its mixture with the zero gas being changed and by comparing the results in the two stages, the oxygen concentration in the sample gas can be calculated on a real-time basis. Once analysis of the sample gas has started, there is no need to perform frequent zero adjustment as in the prior art.

Both the proportion of the sample gas in the first gas mixture and that of the zero gas in the second gas mixture are preferably adjusted to lie in the range of 10–30%. To give just one example, the flow ratio between the zero gas and the sample gas is 80:20 (mL/min) in the first gas mixture and 20:80 (mL/min) in the second gas mixture. The greater the difference between the oxygen concentration in the first gas mixture and that in the second gas mixture, the higher the precision in the measurement of oxygen concentration in the sample gas. On the other hand, if the oxygen concentration in the sample gas is unduly low, a relatively large amount of impurities in air will get into the gas feed line through connections such as valves and joints and the precision in measurement will decrease. Therefore, both the proportion of the sample gas in the first gas mixture and that of the zero gas in the second gas mixture are preferably adjusted to lie in the range of 10–30%.

Figure 3:
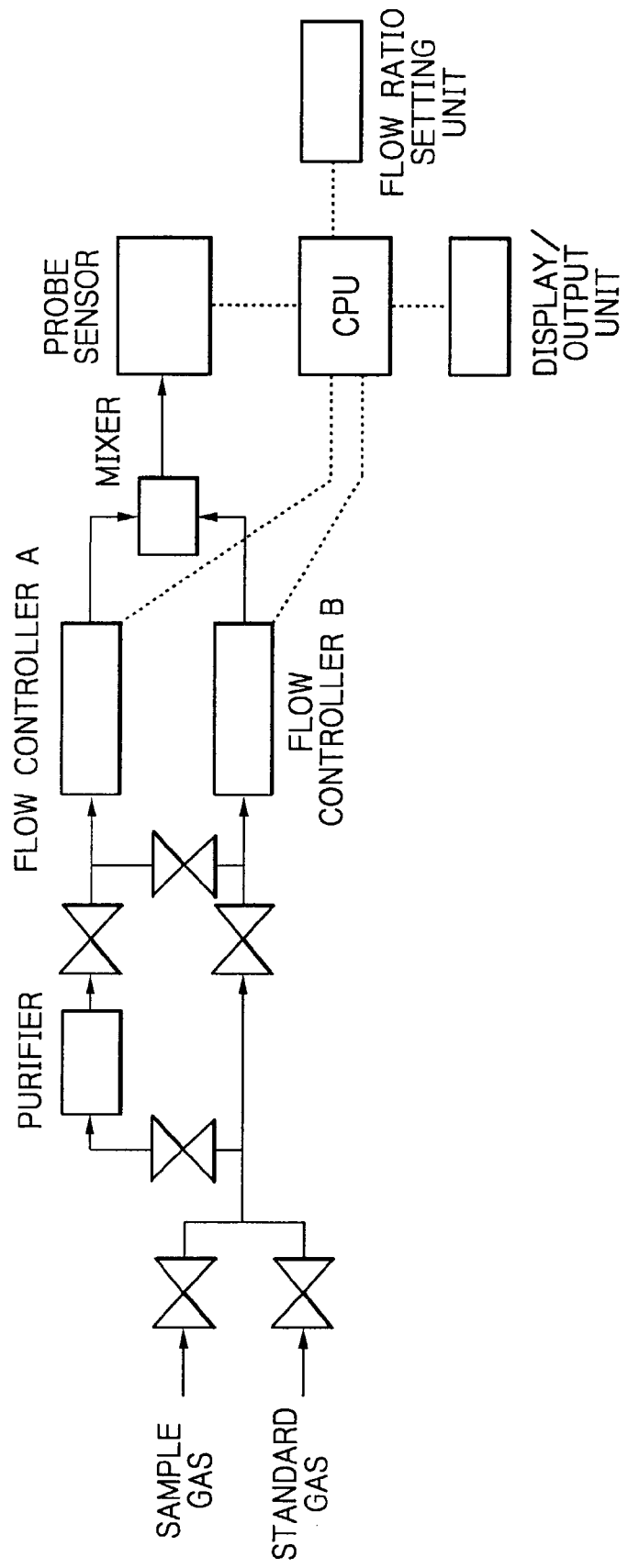
FIG. 3 is a block diagram showing a specific preferred configuration of the oxygen concentration analyzer of the invention.
Figure 4:
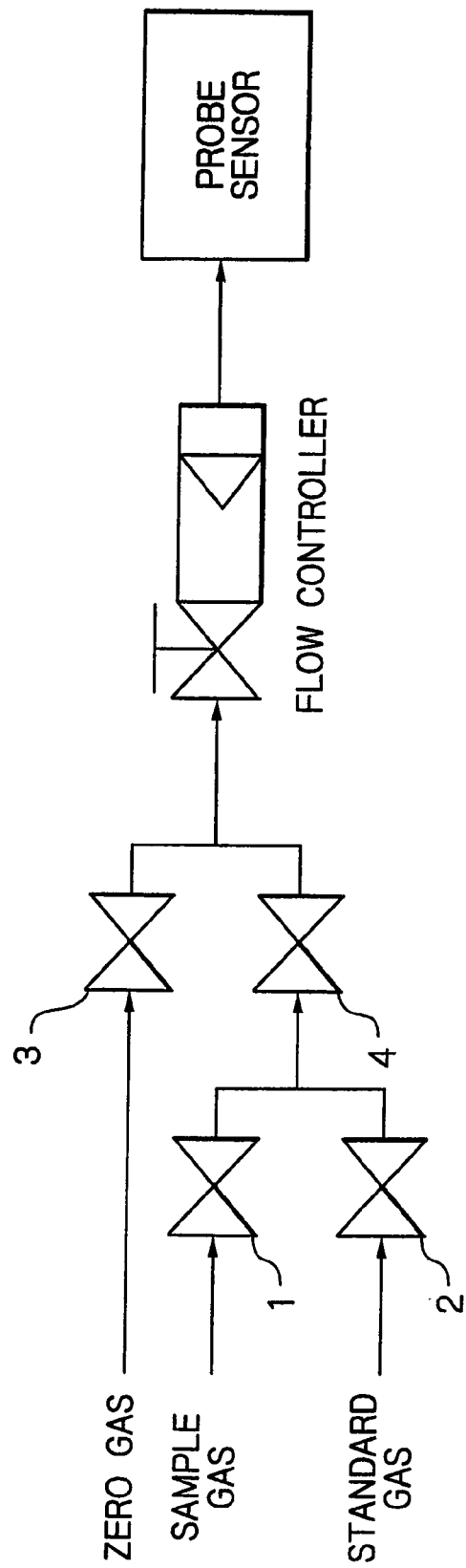
FIG. 4 is a block diagram showing the configuration of a conventional oxygen concentration analyzer.

A preferred configuration of the oxygen concentration analyzer according to the invention is shown in block form in FIG. 3. The configuration shown in FIG. 3 is basically the same as shown in FIG. 1, except that the line for selectively feeding the standard gas and the sample gas has a branch which connects to a purifier for removing oxygen from the sample gas to prepare the zero gas. Each of the flow controllers A and B consists of a flow measuring section, a signal output section and a flow controlling section. The flow controllers may be of any type such as a mass flow controller or a combination of a flow control valve, an orifice flow meter and a flow indicator/adjuster.

The system shown in FIG. 3 is also furnished with a device that performs computer-controlled monitoring on external output signals from the flow measuring sections in the flow controllers A and B for the flows of the zero gas and the sample gas, respectively, and which controls them automatically to have the flow ratios set in a flow ratio setting unit. The heart of this device is a CPU (central processing unit) to which the flow controllers A and B, the probe sensor, the gas flow ratio setting unit and a display/output unit are connected via control/measuring signal lines indicated by dotted lines. The sequence of automatic output signal control is as follows: 1) in order to ensure that the flows of the zero gas and the sample gas in the first stage and those in the second stage become equal to specified settings in the flow ratio setting unit, the CPU monitoring the outputs from the flow controllers A and B controls the inputs to the flow ratio setting unit by changing them; 2) the gas mixture from the mixer is introduced into the probe sensor and the measured signal output from the sensor is checked with the CPU; 3) when the output of the sensor has stabilized, its output in the first stage is stored in a memory; 4) the first stage is switched over to the second stage and when the output of the sensor has stabilized, its output in the second stage is stored in the memory; 5) from the stored sensor outputs and the flows of the zero gas and the sample gas in the first and second stages (i.e., the proportions of the sample gas in its mixture with the zero gas as found in the first and second stages), the CPU calculates the oxygen concentration in the sample gas using the calibration curve (i.e., Eq. 2); 6) the calculated value is represented on the display unit and delivered to the output unit; 7) steps 3)–6) are repeated to perform measurement.

EXAMPLE

Figure 5:
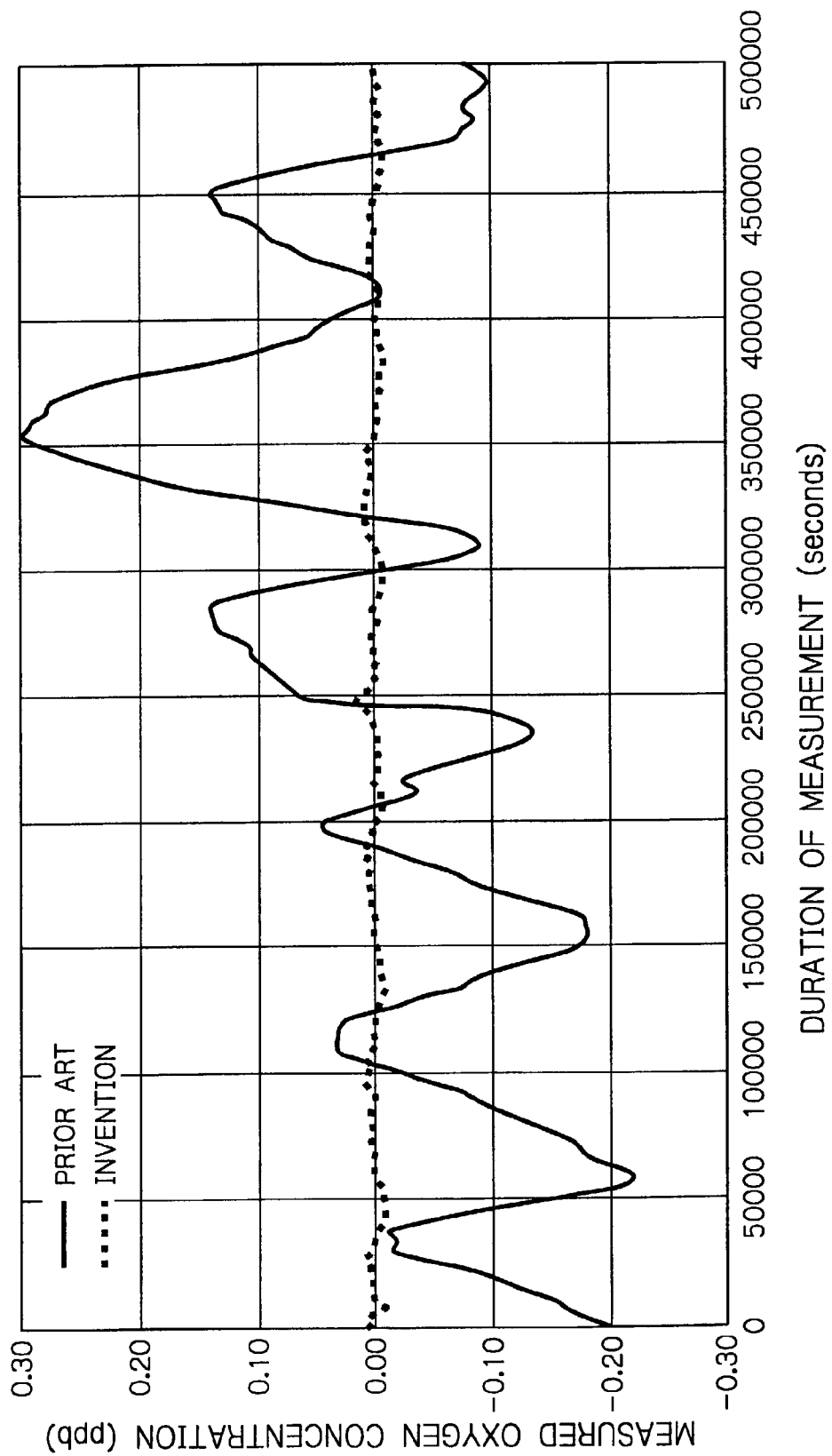
FIG. 5 is a graph showing the results of a test conducted to evaluate the stability of oxygen concentration measurements obtained by the analytical method of the invention and a prior art method.

Using an analyzer of the type shown in FIG. 3, a test was conducted to check the stability of oxygen concentration measurements obtained by the analyzing method of the invention. A Galvanic cell type oxygen concentration analyzer was used as the probe sensor. A zero gas prepared by passing nitrogen gas through the purifier was passed into the flow controller A. Similarly, nitrogen gas was passed through another purifier to make a sample gas which was passed into the flow controller B. Nitrogen gas substantially free of oxygen was used as the sample gas in order to check to see if measurements of oxygen concentration would constantly register 0 ppm. In the first stage, the zero gas was flowed at a rate of 80 mL/min and the sample gas at a rate of 20 mL/min; the two gases were mixed in the mixer and the resulting gas mixture was introduced into the probe sensor at a rate of 100 mL/min. In the second stage, the zero gas was flowed at a rate of 20 mL/min and the sample gas at a rate of 80 mL/min. With the first stage being switched to the second stage and vice versa at 10-min intervals, the oxygen concentration in the sample gas was measured in a time period between 0 and $50 \times 10^4$ seconds (for ca. 139 hours). The result is shown graphically in FIG. 5 by a thin dashed line; the value of 0.00 ppb was maintained constantly. It is therefore clear that precise measurement can be made consistently even if oxygen-containing nitrogen gas that was not passed through the purifier is supplied as the sample gas.

As a comparison, a prior art method of analysis was performed in the following manner: substantially oxygen free nitrogen gas that was prepared by the same method as described above was passed into a third flow controller via a line branching at a position upstream of the flow controller B and from that third flow controller, the sample gas was introduced into another Galvanic cell type oxygen concentration sensing probe. The result of oxygen concentration measurement in a time period between 0 and $50 \times 10^4$ seconds is shown graphically in FIG. 5 by thick solid lines. The measured values varied greatly between −0.20 to 0.30 ppb. The variation was cyclic at a period of about 86,000 seconds (ca. 24 hours), suggesting the effect of the changes in ambient temperature.

What is claimed is:

1. A method for analyzing the oxygen concentration of a gas with an oxygen concentration analyzer of such a type that a probe sensor, when supplied with a gas to be analyzed, produces an electrical output which is proportional to the concentration of oxygen in the gas, the method comprising the steps of:

preparing a first gas mixture of an oxygen-free gas and a sample gas mixed at a predetermined flow ratio and a second gas mixture of the oxygen-free gas and the sample gas mixed at a different flow ratio than in the first gas mixture;

passing the first gas mixture and the second gas mixture sequentially into the probe sensor and obtaining a first and a second electrical output, respectively; and comparing the electrical outputs from the sensor for the first gas mixture and the second gas mixture, and comparing the proportions of the flow of the sample gas in the first gas mixture and the second gas mixture to thereby calculate the oxygen concentration in the sample gas.

2. The method according to claim 1, wherein a proportional expression for the relationship between an electrical output from the probe sensor and the oxygen concentration of gas is preliminarily determined using the oxygen-free gas and a standard gas of a known oxygen concentration and the electrical outputs from the sensor for the first gas mixture and the second gas mixture, and the proportions of the flow of the sample gas in the first gas mixture and the second gas mixture are substituted into the proportional expression to thereby calculate the oxygen concentration in the sample gas.

3. The method according to claim 1, wherein the first gas mixture and the second gas mixture are alternately passed into the probe sensor without interruption and both the proportion of the flow of the sample gas in the first gas mixture and the proportion of the flow of the oxygen-free gas in the second gas mixture are adjusted to lie between 10 to 30%.

4. The method according to claim 1, wherein the electrical output for the measurement of the flows of oxygen-free gas and the sample gas in each of the first second gas mixtures are monitored with a computer and automatically controlled to specified settings of gas flow and flow ratio.

5. The method according to claim 1, wherein the oxygen concentration analyzer is of a type that relies on such a principle that when oxygen in the sample gas reacts with an electrolyte on the surface of an electrode contained in the sensor probe, an electric current flows between the electrodes in the sensor probe in an amount that is proportional to the oxygen concentration in the sample gas.

6. The method of claim 1, wherein the oxygen concentration of the sample gas is calculated by determining the difference between the electrical output of the first gas mixture and the electrical output of the second gas mixture.

7. The method of claim 6, wherein the oxygen concentration of the sample gas is calculated by the flow of the sample gas in the first gas mixture and the flow of the sample gas in the second gas mixture.

8. The method of claim 1, wherein the oxygen concentration of the sample gas is calculated by the equation $$x = (y_1 - y_2)/a(S_1 - S_2)$$

where (a) is a constant, x is the oxygen concentration of the sample gas, $y_1$ and $y_2$ are the probe sensor output signals for the first gas mixture and the second gas mixture, respectively, $S_1$ is the ratio of the flow of the sample gas to the flow of the first gas mixture, and $S_2$ is the ratio of the flow of the sample gas to the flow of the second gas mixture.

* * * * *